_United States Patent_ [19]

Löbermann

[11] Patent Number: 4,990,597
[45] Date of Patent: Feb. 5, 1991

[54] PROCESS FOR THE PURIFICATION OF PLACENTAL TISSUE PROTEIN PP4

[75] Inventor: Hartmut Löbermann, Schallstadt, Fed. Rep. of Germany

[73] Assignee: Behringwerke Aktiengesellschaft, Marburg/Lahn, Fed. Rep. of Germany

[21] Appl. No.: 222,998

[22] Filed: Jul. 22, 1988

[30] Foreign Application Priority Data

Jul. 25, 1987 [DE] Fed. Rep. of Germany ....... 3724726

[51] Int. Cl.$^5$ .......................... C07K 3/18; C07K 3/20; C07K 3/22
[52] U.S. Cl. ..................................... 530/392; 530/395; 530/399; 530/412; 530/415; 530/416; 530/851; 530/417; 536/59
[58] Field of Search ............... 530/395, 392, 399, 412, 530/416, 851, 415, 417; 536/59; 424/101

[56] References Cited

U.S. PATENT DOCUMENTS

| | | | |
|---|---|---|---|
| 4,178,439 | 12/1979 | Ayers et al. | 536/59 |
| 4,507,229 | 3/1985 | Bohn | 530/392 |
| 4,603,010 | 7/1986 | Ayers et al. | 530/359 |
| 4,732,891 | 3/1988 | Maki et al. | 530/416 X |
| 4,736,018 | 4/1988 | Reutelingsperger | 530/412 X |

OTHER PUBLICATIONS

H. Bohn et al., Arch. Gynecol., vol. 236, pp. 225–233 (1985).
L. Sundberg et al., J. Chromatogr., vol. 90, pp. 87–98 (1974).

_Primary Examiner_—Howard E. Schain
_Attorney, Agent, or Firm_—Finnegan, Henderson, Farabow, Garrett, and Dunner

[57] ABSTRACT

A process for the purification of tissue protein PP4 which can be obtained from placenta is described.

This process makes use of the property of binding to saccharide polysulfates or to sulfated sugars in the presence of calcium ions.

10 Claims, No Drawings

PROCESS FOR THE PURIFICATION OF PLACENTAL TISSUE PROTEIN PP4

The invention relates to a process for the purification of placental tissue protein PP4, which has anticoagulant properties.

Tissue protein PP4 is described in DE No. 33 15 000 A 1 (U.S. Pat. No. 4,507,229) with the following parameters:
- an electrophoretic mobility in the range between those of alpha$_1$ and alpha$_2$ globulins;
- an isoelectric point of 4.85±0.15;
- a sedimentation coefficient $s_{20}^0,_w$ of 3.3±0.2S;
- a molecular weight determined in sodium dodecyl sulfate (SDS)-containing polyacrylamide gel of 35,000±5,000;
- an extinction coefficient $E_{1\,cm}^{1\%}$ (280 nm) of 5.9±0.6;
- a carbohydrate content of 2.4±0.94% (g/100 g) (mannose 0.3±0.2%, galactose 0.4±0.2%, xylose 0.1±0.04%, glucose 0.2±0.1%, glucosamine 1.0±0.2%, neuraminic acid 0.4±0.2%) and the following amino acid composition:

| Amino acid | Residues per 100 residues (mol %) | Coefficient of variation |
| --- | --- | --- |
| Lysine | 6.95 | 1.14 |
| Histidine | 0.97 | 17.40 |
| Arginine | 5.44 | 1.77 |
| Aspartic acid | 11.41 | 1.68 |
| Threonine | 6.78 | 2.40 |
| Serine | 6.21 | 2.26 |
| Glutamic acid | 12.25 | 0.43 |
| Proline | 1.96 | 6.20 |
| Glycine | 6.68 | 3.83 |
| Alanine | 7.92 | 1.67 |
| Cystine ½ | 0.77 | 19.50 |
| Valine | 5.34 | 3.80 |
| Methionine | 1.98 | 6.00 |
| Isoleucine | 5.21 | 2.23 |
| Leucine | 11.50 | 0.45 |
| Tyrosine | 3.55 | 4.21 |
| Phenylalanine | 4.07 | 3.77 |
| Tryptophan | 0.93 | 23.90 |

The processes to date for the purification of PP4, such as, for example, immunoadsorption, gel filtration etc. (Bohn et al., 1985, Arch. Gynaecol. 236, 225–233) are unsuitable for isolation of PP4 on an industrial scale.

Hence the object of the invention was to develop a process for the purification of PP4.

It has now been found, surprisingly, that PP4 exhibits, in the presence of calcium ions, affinity for saccharide polysulfates or for sulfated sugars and can be bound to carrier-bound saccharide polysulfates or sulfated sugars.

Thus the invention relates to a process for the purification of PP4, which comprises contacting a PP4-containing solution, in the presence of calcium ions, with a carrierbound saccharide polysulfate or a sulfated sugar, removing the supernatant liquid, where appropriate washing the carrier matrix loaded with PP4, and eluting PP4.

Examples of carrier matrices which are insoluble in water and to which a saccharide polysulfate or a sulfated sugar can be covalently bonded are insoluble agarose, dextran, polyacrylamide or copolymers of polyethylene glycol, pentaerythritol and methacrylate, or else combinations thereof.

The coupling of a saccharide polysulfate or sulfated sugar to a carrier of this type can be carried out by known methods, for example by reaction with a carrier resin which has previously been activated with CNBr or epoxide, or via carbodiimide coupling to an aminofunctionalized carrier resin.

In a preferred procedure, a PP4-containing solution of pH 5.5–9.5, which preferably contains 0.01–50 mg of PP4/ml of solution and 0.001–0.2 mol/l calcium ions, for example in the form of calcium chloride, calcium acetate or calcium lactate, is contacted with a carrier-bound saccharide polysulfate or carrier-bound sulfated sugar, for example carrier-bound heparin, dextran sulfate, heparin sulfate, chondroitin sulfate, keratan sulfate or dermatan sulfate, the supernatant solution is removed, the carrier material loaded with PP4 is, where appropriate, washed with a buffer of pH 5.5–9.5 which contains 0.001–0.2 mol/l calcium ions and 0.001–0.4 mol/l of a salt for example NaCl, KCl or LiCl, and PP4 is eluted by stepped or gradient elution with the salt concentration being increased.

In a particularly preferred procedure, a PP4-containing solution of pH 7.0–9.0, which contains 0.003–0.02 mol/l calcium ions, is contacted with carrier-bound heparin or dextran sulfate, but very particularly preferably with carrier-bound heparin, the mixture is incubated, for example at 4°–30° C. for 5–300 min, the supernatant solution is separated from the carrier resin loaded with PP4, where appropriate washing with a solution of pH 7.0–9.0, which contains 0.003–0.02 mol/l calcium ions and 0.05–0.3 mol/l NaCl, KCl or LiCl, is carried out, and PP4 is washed off the carrier resin by increasing the salt concentration to 0.35–1.5 mol/l by means of a stepped or gradient elution.

It is also possible, where appropriate, to follow with, for example, rechromatography on another carrier-bound saccharide polysulfate or carrier-bound sulfated sugar.

The process according to the invention is distinguished by allowing PP4 to be isolated in a few steps in very high purity and yield even on the industrial scale.

The examples which follow are intended to illustrate the invention.

EXAMPLE 1

3 l of a phenyl-$^R$Sepharose eluate which had been prepared as in Example 1 of DE-A-36 43 182 (160 μg of PP4/ml) were dialyzed against buffer A (50 mmol/l Tris/HCl, 25 mmol/l NaCl, 5 mmol/l CaCl$_2$, pH 8.0). The solution was mixed in a batch process with 300 ml of a heparin-$^R$Sepharose (from Pharmacia, Uppsala, Sweden, Order No. 17-0467-01) and stirred at room temperature for 30 min, and the supernatant solution was removed. The adsorbent was then washed with buffer A, and PP4 was eluted by a stepped NaCl gradient (180 mmol/l, 3000 mmol/l and 1.5 mol/l NaCl). It is possible, where appropriate for further purification, to rechromatograph the resulting PP4 material on a dextransulfate-$^R$Sepharose in buffer A without CaCl$_2$. SDS polyacrylamide gel electrophoresis of the PP4 purified in this way produced one band with a molecular weight of about 32 kDa.

EXAMPLE 2

1 l of phenyl-$^R$Sepharose eluate (as Example 1) was dialyzed against buffer A. The dialysate was applied to 200 ml of dextran-sulfate-$^R$Sepharose (epoxy-activated Sepharose 6B, dextran sulfate from Pharmacia, Uppsala, Sweden, Order Nos. 17-0480-01, 17-0340-01; coupling of the substances was by known methods, for example that of Sundberg, L., Porath, J. (1974), J. Chromatogr. 90, 87-98.), which had been equilibrated with buffer A, and was washed. PP4 was eluted using an NaCl gradient. The PP4-containing fractions were dialyzed against buffer A and then rechromatographed, for example on a heparin-$^R$Sepharose. SDS polyacrylamide gel electrophoresis of the PP4 material produced one band with a molecular weight of about 32 kDa.

I claim:

1. A process for the purification of PP4, which comprises contacting a PP4-containing solution, in the presence of calcium ions, with a carrier-bound saccharide polysulfate or a sulfated sugar, removing the supernatant liquid, and eluting PP4.

2. The process as claimed in claim 1, wherein the carrier material is insoluble agarose, dextran, polyacrylamide, an amino-functionalized carrier resin or a copolymer of polyethylene glycol, pentaerythritol and methacrylate, or a combination of these.

3. The process as claimed in claim 1, wherein the saccharide polysulfate is heparin, dextran sulfate, heparin sulfate, chondroitin sulfate, keratan sulfate or dermatan sulfate.

4. The process as claimed in claim 1, wherein carrier-bound heparin or dextran sulfate is used.

5. The process as claimed in claim 1, wherein 0.001-0.2 mol/l calcium ions are present.

6. The process as claimed in claim 1, wherein carrier-bound heparin, dextran sulfate, heparin sulfate, chondroitin sulfate, keratan sulfate or dermatan sulfate is used.

7. The process as claimed in claim 1, wherein a buffer of pH 5.5-9.5, which contains 0.001-0.2 mol/l calcium ions and 0.001-0.4 mol/l NaCl, KCl or LiCl, is used for washing.

8. The process as claimed in claim 1, further comprising, after removing the supernatant liquid and before eluting PP4, washing the carrier matrix loaded with PP4.

9. The process as claimed in claim 4, wherein carrier-bound heparin is used.

10. The process as claimed in claim 7, wherein 0.003-0.02 mol/l calcium ions and 0.05-0.3 mol/l NaCl, KCl or LiCl is used for washing.

* * * * *